United States Patent [19]

Frohn et al.

[11] Patent Number: 5,728,896

[45] Date of Patent: Mar. 17, 1998

[54] PROCESS FOR THE PREPARATION OF HYDROXYMETHYL-CYCLOPROPANE

[75] Inventors: Lutz Frohn, Erkrath; Reinhard Langer; Gerhard Darsow, both of Krefeld; Eberhard Zirngiebl, Köln; Jörg-Dietrich Jentsch, Mülheim a.d. Ruhr; Bernd Pennemann; Christoph Tiburtius, both of Köln, all of Germany

[73] Assignee: Bayer Aktiengesellschaft, Leverkusen, Germany

[21] Appl. No.: 601,931

[22] Filed: Feb. 15, 1996

[30] Foreign Application Priority Data

Feb. 21, 1995 [DE] Germany .................... 195 05 939.5

[51] Int. Cl.$^6$ .................................................. C07C 29/136
[52] U.S. Cl. .................................................. 568/700
[58] Field of Search .................................................. 568/700

[56] References Cited

U.S. PATENT DOCUMENTS

| 2,358,234 | 9/1944 | Lazier et al. | 260/100 |
| 4,720,597 | 1/1988 | Otte et al. | 568/814 |

FOREIGN PATENT DOCUMENTS 0222988   5/1987   European Pat. Off. .

OTHER PUBLICATIONS

Encyclopaedia Britannica, 15th edition, vol. 1, p. 270.

*Primary Examiner*—S. Mark Clardy
*Assistant Examiner*—Barbara Badio
*Attorney, Agent, or Firm*—Sprung Kramer Schaefer & Briscoe

[57] ABSTRACT

Hydroxymethyl-cyclopropane (cyclopropyl-methanol) can be obtained in a manner which is both economical and environment-friendly by catalytic hydrogenation of cyclopropanecarboxylic acid alkyl esters under increased pressure at elevated temperature if a chromium-free zinc oxide catalyst is employed as the catalyst.

12 Claims, No Drawings

PROCESS FOR THE PREPARATION OF HYDROXYMETHYL-CYCLOPROPANE

The present invention relates to a process for the preparation of hydroxymethyl-cyclopropane (cyclopropyl-methanol) by hydrogenation of alkyl esters of cyclopropanecarboxylic acid in the presence of a chromium-free catalyst comprising zinc oxide.

Hydroxymethyl-cyclopropane is used as a synthesis unit in the preparation of medicaments and plant protection agents.

It is known from U.S. Pat. No. 4,720,597 that hydroxymethyl-cyclopropane can be obtained by catalytic hydrogenation of cyclopropanecarboxylic acid esters. Although this process gives considerably improved yields compared with processes of the prior art mentioned in this U.S. patent, it is necessary to employ a Zn—Cr catalyst, which is characterized by the high toxicity of the Cr compound used.

There was therefore the need to develop a hydrogenation process for the preparation of hydroxymethyl-cyclopropane from cyclopropanecarboxylic acid esters which is both economical and environment-friendly and, in particular, can be carried out without highly toxic Cr compounds. It has now been found, surprisingly, that both aims can be achieved by the use of a Zn-containing catalyst with which the toxic Cr can be dispensed with.

The invention relates to a process for the preparation of hydroxymethyl-cyclopropane from cyclopropanecarboxylic acid $C_1$–$C_{10}$-alkyl esters, which is characterized in that the cyclopropanecarboxylic acid esters are hydrogenated with excess hydrogen in the presence of a chromium-free catalyst comprising zinc oxide under 50 to 350 bar at 150° to 350° C.

Cyclopropanecarboxylic acid alkyl esters for the process according to the invention are those in which the alkyl radical has 1 to 10 C atoms, for example methyl, ethyl, propyl, isopropyl, butyl, isobutyl, pentyl, hexyl, octyl or decyl, preferably $C_1$–$C_8$-alkyl radicals of the type mentioned, particularly preferably $C_1$–$C_4$-alkyl radicals of the type mentioned.

The pressure range for the process according to the invention is from 50 to 350 bar, preferably 180 to 350 bar, particularly preferably 190 to 300 bar.

The temperature range for the process according to the invention is from 150° to 350° C., preferably 250° to 325° C., particularly preferably 270° to 325° C.

It is possible for the process according to the invention to be carried out without the use of a solvent or solvent mixture, but the presence of a solvent or solvent mixture which is stable under the reaction conditions is also possible, it being possible for solvents familiar to the expert to be employed for such applications. Since the presence of such solvents makes working up difficult, the reaction is preferably carried out without the presence of such solvents.

It is possible according to the invention for any distillation refluxes, for example with a content of cyclopropanecarboxylic acid esters which have not been hydrogenated completely, to be recycled into the reaction.

The process according to the invention can be carried out either discontinuously or continuously. The apparatuses required for carrying out the process are known in the prior art and familiar to the expert. Examples which may be mentioned are: two-phase reactors with a fixed or agitated catalyst bed, the catalyst forming the solid phase and the other components (educt, products and $H_2$) being in the gas phase, and multi-phase reactors in which one or more liquid phases are present, in addition to the solid and the gaseous phase, such as, for example, a gassed stirred tank, bubble column, liquid phase reactor or trickle phase reactor. The process according to the invention can be carried out particularly advantageously in a continuous manner. This is advantageously effected by passing the liquid starting material over the catalyst arranged in piece form in the reactor, for example in accordance with the trickle phase principle, while the hydrogen is passed in co- or countercurrent through the reaction tube. The hydrogen employed in excess (1 to 500 molar excess) is advantageously circulated. The process according to the invention is particularly preferably carried out in the gas phase. Comparable hydrogenation processes and their implementation according to the choice of conditions, for example the temperature, pressure and molar ratio of educt: hydrogen, are known to the expert.

The process according to the invention is characterized by the use of a chromium-free catalyst comprising zinc oxide. The zinc oxide can be obtained by any method and manner known to the expert, for example by combustion of metallic zinc or by treatment of aqueous solutions of zinc salts with bases. A zinc oxide precipitated in this way is dried. The zinc oxide can be employed both in the form obtained and after one or more further processing steps. Thus, zinc oxide in powder form is preferred for use in suspension phases, while it is advantageous to convert the zinc oxide into piece form for trickle phase and gas phase reactors. In this case, for example, the moist precipitate obtained by precipitation of zinc salt solutions is kneaded thoroughly in a kneader and processed to shaped pieces in a granulating apparatus. The still moist shaped articles are then calcined at 300° to 500° C. for 1 to 10 hours. Equally, however, the zinc oxide catalyst can also be absorbed onto a support known to the expert, such as $SiO_2$, $Al_2O_3$, $TiO_2$, $ZrO_2$, MgO and the like, or pressed and granulated with the aid of a binder (tabletting auxiliary). Based on the use of pure zinc oxide (100%), the content of ZnO in the catalyst is 20–100%, preferably 50–100% of the total catalyst weight. The amount of tabletting auxiliary, for example graphite, is 0–20% of the total catalyst weight, based on its emission (0%).

Zinc oxide is an active substance with regard to the process according to the invention, the activity of which can also be acquired, modified or increased by mixing with other solids. To increase the activity of this catalyst, it may be advantageous to add further components, such as, for example, compounds of sodium, potassium, magnesium, calcium, vanadium, niobium, tantalum, molybdenum, iron, ruthenium, cobalt, rhodium, nickel, palladium, platinum, rhenium, copper or silver, in an amount of 1–30 g atom %, calculated as the metal on which the component is based and based on the g atom amount of Zn. These components can be applied in any manner known to the expert, for example by simultaneous or separate precipitation and subsequent bringing together or by impregnation of the zinc oxide with compounds dissolved in water or other liquids and subsequent drying.

Additions of copper have proved to be particularly suitable.

Pure zinc oxide having an internal surface area of more than 10 $m^2/g$ (BET), particularly preferably more than 35 $m^2/g$ and up to 150 $m^2/g$, if appropriate on a support or diluted with inert materials, is preferably employed.

EXAMPLES

Example 1

4 g of methyl cyclopropanecarboxylate and 80 Nl of hydrogen per hour are passed through a reaction tube filled with 40 ml of ZnO catalyst (tablets, 5×3 mm). The temperature was 297° C. and the pressure was 300 bar.

The conversion of methyl cyclopropanecarboxylate was 99% and the selectivity for hydroxymethyl-cyclopropane was 92%.

Example 2

Procedure as in Example 1, but ethyl cyclopropanecarboxylate was employed.

The conversion of ethyl cyclopropanecarboxylate was 99% and the selectivity for hydroxymethyl-cyclopropane was 93%.

Example 3

Procedure as in Example 1, but propyl cyclopropanecarboxylate was employed.

The conversion of propyl cyclopropanecarboxylate was 98% and the selectivity for hydroxymethyl-cyclopropane was 90%.

Example 4

Procedure as in Example 1, but butyl cyclopropanecarboxylate was employed.

The conversion of butyl cyclopropanecarboxylate was 99% and the selectivity for hydroxymethyl-cyclopropane was 89%.

Example 5

Procedure as in Example 1, but isobutyl cyclopropanecarboxylate was employed.

The conversion of isobutyl cyclopropanecarboxylate was 99% and the selectivity for hydroxymethyl-cyclopropane was 93%.

Example 6

5.5 g of isobutyl cyclopropanecarboxylate and 300 Nl of hydrogen per hour were passed through a reaction robe filled with 50 ml of ZnO tablets doped with copper (comprising 50 g of copper in the form of copper oxide and/or copper hydroxide per liter of ZnO tablets). The temperature was 207° C. and the pressure was 300 bar.

The conversion of isobutyl cyclopropanecarboxylate was 98% and the selectivity for hydroxymethyl-cyclopropane was 91%.

What is claimed is:

1. A process for the preparation of hydroxymethyl-cyclopropane from a cyclopropanecarboxylic acid $C_1$–$C_{10}$-alkyl ester, in which the cyclopropanecarboxylic acid ester is hydrogenated with excess hydrogen in the presence of a chromium-free catalyst comprising zinc oxide under 50 to 350 bar at 150° to 350° C.

2. The process of claim 1, in which the hydrogenation is carried out under 180 to 350 bar.

3. The process of claim 1, in which the hydrogenation is carried out at 250° to 325° C.

4. The process of claim 1, in which a cyclopropanecarboxylic acid $C_1$–$C_8$-alkyl ester is employed.

5. The process of claim 1, in which a cyclopropanecarboxylic acid $C_1$–$C_4$-alkyl ester is employed.

6. The process of claim 1, in which Zn oxide is employed as the catalyst.

7. The process of claim 1, in which the hydrogenation is carried out in the gas phase, the hydrogen being passed in cocurrent.

8. The process of claim 1, in which the hydrogeration is carried out in the trickle phase, the hydrogen being passed in cocurrent.

9. The process of claim 1, in which the hydrogenation is carried out in the gas phase, the hydrogen being passed in countercurrent.

10. The process of claim 1, in which the hydrogenation is carried out in the trickle phase, the hydrogen being passed in countercurrent.

11. The process according to claim 1, in which the hydrogenation is carried out in the gas phase.

12. The process of claim 1, in which Zn oxide with an addition of copper is employed as the catalyst.

* * * * *